US00PP29471P3

(12) United States Plant Patent
Bourne

(10) Patent No.: US PP29,471 P3
(45) Date of Patent: Jul. 10, 2018

(54) GRAPEVINE NAMED 'SV21-61-373'

(50) Latin Name: *Vitis vinifera*
Varietal Denomination: SV21-61-373

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 107 days.

(21) Appl. No.: 15/330,485

(22) Filed: Sep. 26, 2016

(65) Prior Publication Data

US 2017/0105324 P1 Apr. 13, 2017

(51) Int. Cl.
*A01H 5/08* (2018.01)

(52) U.S. Cl.
USPC ..... Plt./207

(58) Field of Classification Search
USPC ..... Plt./207
See application file for complete search history.

*Primary Examiner* — Anne Marie Grunberg
(74) *Attorney, Agent, or Firm* — Baker Manock & Jensen, PC; Eric C. Cole

(57) ABSTRACT

A new and distinct variety of grapevine plant named 'SV21-61-373' particularly characterized by its green berry color, very firm texture and very large, sweet berries. Additionally, berries of the new cultivar are very responsive to applications of exogenous gibberellic acid and trunk girdling, more than doubling in size in comparison to untreated fruit.

2 Drawing Sheets

Latin name of genus and species: The plant claimed relates to a new and distinct variety of *Vitis vinifera.*

Variety denomination: The plant claimed shall be known as 'SV21-61-373'.

STATEMENT REGARDING FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV21-61-373'. As used herein, 'grapevine' refers to all plant parts including, vines, canes, tendrils, leaves, fruit and roots of 'SV21-61-373'. Grapevine named 'SV21-61-373' is the result of an effort to produce a late ripening, green, seedless table grape with fruit characteristics superior to currently available green grape cultivar 'Thompson Seedless' (unpatented) and 'Autumn King' (U.S. Plant Pat. No. 16,284). This new cultivar originated from a cross conducted in May 2000 near McFarland, Calif. between pistillate grapevine plant selection '13-2-138' (unpatented) and pollen parent 'SV9-9-12' (unpatented). Resultant ovules from the cross were harvested 42 days after pollination and cultured on agar substrate containing 'McCown's Woody Plant Medium'. Embryonic plants were dissected from those cultured ovules after twelve weeks and were transferred to culture tubes containing the same medium in the laboratory under twelve hours of light from standard fluorescent lamps at 27° C. The seedlings from this effort were transplanted to the greenhouse in November of 2000 and grown in the greenhouse at 29° C. with 12 hours illumination under high pressure sodium vapor lamps. The seedling population of 496 plants was planted in the field in the spring of 2002 near Delano, Calif. The new grapevine was selected from this seedling population on Sep. 19, 2005. It was then propagated by cuttings and grafted to 'Freedom' (unpatented) rootstock in 2006. The present invention has been found to retain its distinctive characteristics through four successive asexual propagations.

Grapevine named 'SV21-61-373' differs from the female parent grapevine 'SV13-2-138' (unpatented) in that 'SV21-61-373' has ovate shaped, seedless berries and flowers with functional pollen, whereas 'SV13-2-138' has spherical shaped berries with partially lignified seed traces and flowers that are pistillate (functionally female).

Grapevine named 'SV21-61-373' differs from its male parent, 'SV9-9-12' (unpatented) in that 'SV21-61-373' has ovate shaped, bright green berries that do not brown internally while in cold storage, whereas 'SV9-9-12' has oblong shaped, green berries.

Grapevine named 'SV21-61-373' differs from the commercial cultivar 'Thompson Seedless' in that 'SV21-61-373' has ovate shaped, bright green berries, whereas 'Thompson Seedless' has elongate shaped, light green berries. The berries of 'SV21-61-373' have a superior eating quality and larger berries at harvest after standard vineyard practices of application of exogenous gibberellic acid and girdling of the vine trunks as compared to 'Thompson Seedless'. Additionally, 'SV21-61-373' has fruitful shoots with spur pruning to two buds, whereas 'Thompson Seedless' lacks fruitfulness with spur pruning.

SUMMARY OF THE INVENTION

The following are the most outstanding and distinguishing characteristics of this new variety when grown under normal horticultural practices near McFarland, Calif.:

1. Green skinned;
2. Very firm berry texture; and
3. Very large, ovate shaped berries with sweet taste.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from a plant about 8 years-old, grown in a field near McFarland, Calif. in 2015.

FIG. 1 Fruit clusters on the vine.

FIG. 2 Natural fruit cluster on left, gibberellic acid treated fruit cluster on the right with shoots, leaves and tendrils.

DETAILED BOTANICAL DESCRIPTION

The following detailed description sets forth the distinctive characteristics of 'SV21-61-373'. Descriptions of the new invention apply to vines of 'SV21-61-373' grown on 'Freedom' rootstock at a density of 1,537 vines per hectare grown near McFarland, Calif. in 2015. These vines were in their ninth year of full production having been grafted to existing rootstock 'Freedom' in 2006. These descriptions are believed to apply generally to the new variety grown under similar circumstances elsewhere. Color references are primarily to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV21-61-373'.

Plant:

*Vigor*.—Medium; vines spur-pruned and shoot thinned to 32 shoots average 241.5 cm of growth per cane.
*Density of foliage*.—Moderate.
*Productivity*.—Very productive when spur pruned, up to 22,125 kg/hectare.
*Hardiness*.—Hardiness observed to 0° C.
*Rootstock*.—'Freedom' (unpatented).

Trunk:

*Shape*.—Broadly elliptical.
*Straps*.—Long, split.
*Surface texture*.—Shaggy.
*Trunk circumference*.—32.8 cm at 1.0 m of height.
*Inner bark color*.—RHS 166C (greyed orange group).
*Outer bark color*.—RHS 201B (grey group).

Mature leaves:

*Average blade length*.—17.1 cm.
*Average blade width*.—19.5 cm.
*Size of blade*.—Large.
*Shape*.—Pentagonal.
*Anthocyanin coloration of main veins on the upper side of the blade*.—Absent.
*Mature leaf profile*.—Cupped upwards around entire margin.
*Blistering* (*upper surface*).—Absent.
*Leaf blade tip*.—Curved upward.
*Margins*.—Lobed, serrated, undulating.
*Apex*.—Broadly acuminate.
*Bases*.—Sagittate.
*Thickness*.—Medium.
*Undulation of blade between main and lateral veins*.—Slight.
*Shape of teeth*.—Broadly conical, both sides convex.
*Length of teeth*.—7.0 mm to 10.0 mm.
*Ratio length/width of teeth*.—About 1.4:1.
*General shape of petiole sinus*.—Open, conical.
*Tooth at petiole sinus*.—Absent.
*Petiole sinus limited by veins*.—Absent.
*Shape of upper lateral sinus*.—Closed.
*Prostrate hairs between veins* (*lower surface*).—Absent.
*Erect hairs between veins* (*lower surface*).—Dense at vein junctions.
*Prostrate hairs on main veins* (*lower surface*).—Medium, found mostly at vein junctions.
*Density of erect hairs on main veins* (*lower surface*).—Medium.
*Prostrate hairs on main veins* (*upper surface*).—Sparse.
*Upper surface*.—Summer color: RHS 137B (green group). Autumn color: RHS 12B (yellow group). Surface texture: Smooth. Surface appearance: Dull. Goffering of blade: Absent.
*Lower surface*.—Summer color: RHS 137C (green group). Autumn color: RHS 12A (yellow group). Anthocyanin coloration of main veins on lower leaf surface: Absent. Anthocyanin coloration on laterals: Absent. Glossiness: Low. Pubescence: Absent. Surface texture: Smooth. Surface appearance: Shiny.
*Petiole*.—Length: 26.7 cm. Length of petiole compared to middle vein: Petiole about 50% longer than middle vein. Diameter: 3 mm. Density of prostrate hairs: Absent. Density of erect hairs: Absent. Shape of base of petiole sinus: Open; outline is broadly saggitate. Color: In shade: RHS 144A (yellow green group). In sun: RHS N144C (yellow green group).

Tendrils:

*Number*.—Bifurcated and trifurcated; forming at all nodes above node 5.
*Length*.—22.7 cm to 31.5 cm.
*Diameter*.—2.0 mm.
*Texture*.—Smooth.
*Color*.—RHS 144C (yellow green group).

Growing tips (young shoot):

*Pubescence*.—Sparse, prostrate.
*Color*.—RHS 144C (yellow green group).
*Anthocyanins*.—Absent.
*Shape*.—Rounded.
*Apex*.—Fully open.
*Shoot attitude*.—Semi-erect.

Woody shoot:

*Canes*.—Shape: Broadly elliptical. Internode length: About 13.2 cm. Width at node: 1.5 cm. Cross section: Circular. Surface: Smooth. Main color: RHS 165B (greyed orange group). Lenticels: Inconspicuous. Erect hairs on nodes: Absent. Erect hairs on internodes: Absent.
*Laterals*.—Shape: Elliptical. Number: Numerous, forming irregularly above node 5. Length: 42 cm to 121 cm. Diameter: 5.1 mm to 10.1 mm. Internode length: 4.2 cm to 8.0 cm. Color: RHS 165B (greyed orange group).

*Buds*.—Shape: Slightly pointed. Cane bud fruitfulness: Basal buds fruitful, usually 2 clusters per shoot. Length: 5 mm. Width: 7 mm. Height: 6 mm. Color: RHS 166C (greyed orange group). Texture: Smooth.

Flowers:

*Flower sex*.—Perfect.

*Position of first flowering nodes*.—Third or fourth node.

*Number of inflorescences per shoot*.—Usually 2.

*Calyptra color*.—RHS N144A (yellow green group).

*Ovary length*.—3.0 mm.

*Ovary width*.—1.0 mm.

*Ovary color*.—RHS 141A (green group).

*Filament length*.—2.5 mm.

*Filament color*.—Translucent, absence of pigmentation.

*Anther length*.—1.0 mm.

*Anther color*.—RHS 4A (yellow group).

*Date of full bloom*.—May 3.

Fruit:

*Ripening period*.—Around the third week of September at McFarland, Calif.

*Date of ripening*.—September 18 at McFarland, Calif.

*Use*.—Fresh market.

*Keeping quality*.—Very good.

*Shipping quality*.—Good, some clusters have few berries with slight bruising.

*Date of first harvest*.—Sep. 18, 2015.

*Solids-sugar*.—High, about 20 brix at full maturity.

*Refractometer test*.—21.0 brix.

*Cluster*.—

*Bunch*.—Size: Medium. Length (peduncle excluded): About 20.1 cm. Width: About 13 cm. Weight: Natural, without gibberellic acid treatment: 750 g. With gibberellic acid treatment and trunk girdling: 820 g. Density: Well-filled, not compact. Number of berries: 106. Form: Conical.

*Peduncle*.—Length: About 2 cm to 3 cm. Lignification: Medium. Color: RHS 166C (greyed orange group).

*Berry*.—Size: Large. Uniformity of size: Uniform. Weight Natural, without gibberellic acid treatment: About 5 g. With gibberellic acid treatment and trunk girdling: About 15.5 g. Shape: Natural, without gibberellic acid treatment: Ovate. With gibberellic acid treatment: Elliptical-ovate. Presence of seeds: Seedless; most berries developing two to four small, soft rudimentary seeds about 3.0 mm in length. Cross section: Circular. Dimensions: Longitudinal axis: About 2.5 cm. Horizontal axis: About 2.0 cm. Skin color (without bloom): RHS 144A (yellow green group). Coloration of flesh: Translucent; RHS143C (green group). Juiciness of flesh: Very juicy. Berry firmness: Very firm. Particular flavor: Neutral, typical *vinifera*. Bloom (cuticular wax): Medium. Pedicel length: 1 cm. Berry separation from pedicel: With difficulty.

*Skin*.—Thickness: Medium. Texture: Tender. Reticulation: Absent. Roughness: Absent. Tenacity: Tenacious to flesh. Tendency to crack: Resistant.

Disease and insect resistance: Greater susceptibility to powdery mildew (*Erysiphe necator* (Schw.) Burr) has been observed when compared to many other grapes.

Having thus described and illustrated our new variety of grapevine, we claim:

1. A new and distinct variety of grapevine plant named 'SV21-61-373', and parts thereof, substantially as illustrated and described herein.

* * * * *

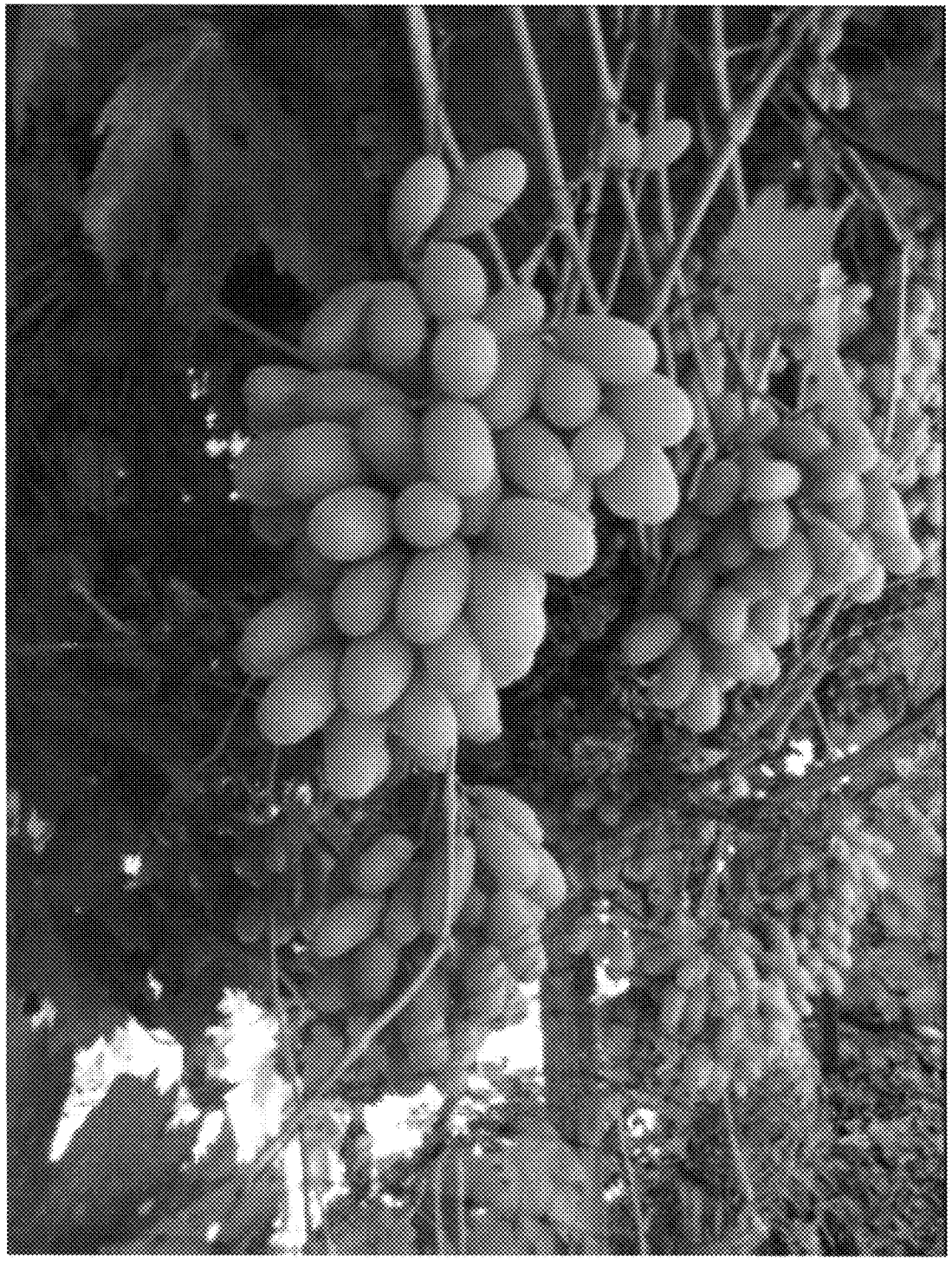

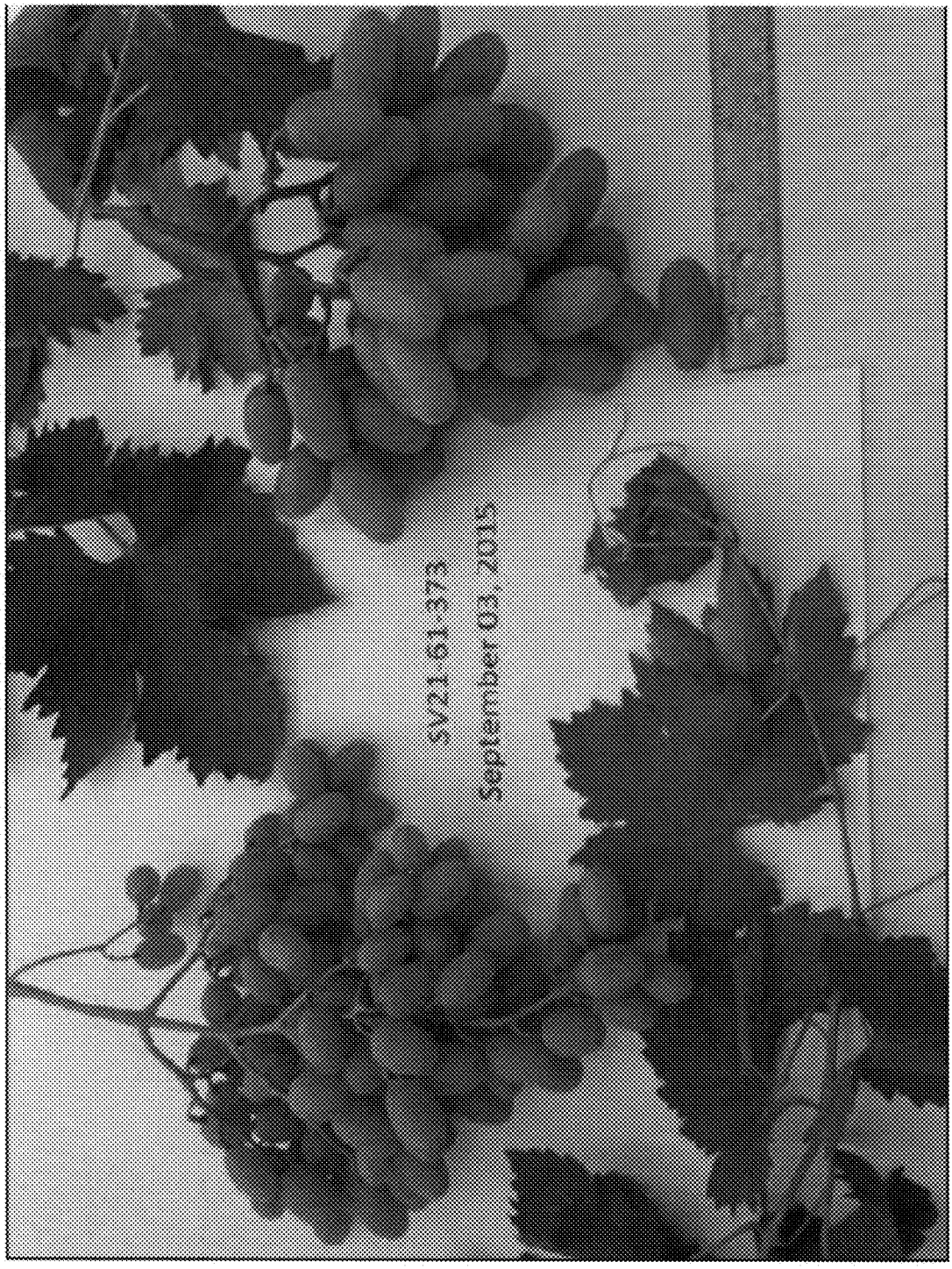
SV21-61-373
September 03, 2016